United States Patent
Woodyer et al.

(10) Patent No.: US 9,491,960 B2
(45) Date of Patent: *Nov. 15, 2016

(54) SWEETENER

(71) Applicant: Tate & Lyle Ingredients Americas LLC, Hoffman Estates, IL (US)

(72) Inventors: Ryan D. Woodyer, Hoffman Estates, IL (US); Jason C. Cohen, Hoffman Estates, IL (US); John R. Bridges, Hoffman Estates, IL (US)

(73) Assignee: Tate & Lyle Ingredients Americas LLC, Hoffman Estates, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/212,152

(22) Filed: Mar. 14, 2014

(65) Prior Publication Data

US 2014/0271746 A1 Sep. 18, 2014

Related U.S. Application Data

(60) Provisional application No. 61/793,502, filed on Mar. 15, 2013.

(51) Int. Cl.
| | |
|---|---|
| *A23L 1/236* | (2006.01) |
| *A23L 2/60* | (2006.01) |
| *A23L 1/09* | (2006.01) |
| *A61K 8/60* | (2006.01) |
| *A61Q 11/00* | (2006.01) |
| *A23L 1/00* | (2006.01) |
| *A61K 47/26* | (2006.01) |
| *A61Q 19/00* | (2006.01) |

(52) U.S. Cl.
CPC ............ *A23L 1/2363* (2013.01); *A23L 1/0047* (2013.01); *A23L 1/09* (2013.01); *A23L 1/2367* (2013.01); *A23L 2/60* (2013.01); *A61K 8/60* (2013.01); *A61K 47/26* (2013.01); *A61Q 11/00* (2013.01); *A61Q 19/00* (2013.01); *A23V 2002/00* (2013.01); *A23V 2200/00* (2013.01); *A23V 2200/16* (2013.01); *A61K 2800/5922* (2013.01)

(58) Field of Classification Search
None
See application file for complete search history.

(56) References Cited

U.S. PATENT DOCUMENTS

| | | |
|---|---|---|
| 4,570,029 A | 2/1986 | Kulprathipanja et al. |
| 4,692,514 A | 9/1987 | Chang |
| 4,880,920 A | 11/1989 | Chang |
| 5,286,499 A | 2/1994 | Courtright |
| 5,411,880 A | 5/1995 | Izumori et al. |
| 5,679,562 A | 10/1997 | Izumori et al. |
| 6,051,236 A | 4/2000 | Portman |
| 7,186,431 B1 | 3/2007 | Silver |
| 8,012,940 B2 | 9/2011 | Nagata |
| 8,030,035 B2 | 10/2011 | Oh et al. |
| 8,216,818 B2 | 7/2012 | Maruta et al. |
| 8,383,183 B2 | 2/2013 | Prakash et al. |
| 8,420,606 B2 | 4/2013 | Izumori et al. |
| 9,049,876 B2 | 6/2015 | Fujihara |
| 2002/0197352 A1 | 12/2002 | Portman |
| 2003/0064135 A1 | 4/2003 | Portman |
| 2004/0143024 A1 | 7/2004 | Yoshino et al. |
| 2005/0013915 A1 | 1/2005 | Riha et al. |
| 2005/0037121 A1 | 2/2005 | Rathjen |
| 2005/0095271 A1 | 5/2005 | Mathewson |
| 2005/0245459 A1 | 11/2005 | Izumori et al. |
| 2007/0020358 A1 | 1/2007 | Mower |
| 2007/0116823 A1 | 5/2007 | Prakash et al. |
| 2008/0221044 A1 | 9/2008 | Tokuda et al. |
| 2008/0260925 A1 | 10/2008 | Zink |
| 2008/0292765 A1 | 11/2008 | Prakash et al. |
| 2009/0068710 A1 | 3/2009 | Izumori et al. |
| 2009/0304891 A1* | 12/2009 | Fujihara ............... A23C 9/13 426/548 |
| 2010/0129865 A1 | 5/2010 | Maruta et al. |
| 2010/0130435 A1 | 5/2010 | Tokuda et al. |
| 2010/0166678 A1 | 7/2010 | Iida et al. |
| 2010/0204346 A1 | 8/2010 | Okuma et al. |
| 2010/0222284 A1 | 9/2010 | Tokuda et al. |
| 2010/0285195 A1 | 11/2010 | Fisher et al. |
| 2010/0285197 A1 | 11/2010 | Fisher et al. |
| 2011/0112043 A1 | 5/2011 | Izumori et al. |
| 2011/0160311 A1 | 6/2011 | Prakash et al. |
| 2011/0237790 A1 | 9/2011 | Lee et al. |
| 2011/0275138 A1 | 11/2011 | Maruta et al. |
| 2011/0318464 A1 | 12/2011 | Prakash et al. |
| 2012/0070534 A1 | 3/2012 | Suzuki |
| 2012/0076893 A1 | 3/2012 | Asayama et al. |
| 2012/0076908 A1* | 3/2012 | Fujihara ............... A23L 1/09 426/548 |
| 2012/0094940 A1 | 4/2012 | Takamine et al. |
| 2012/0244580 A1 | 9/2012 | Hung |
| 2013/0012459 A1 | 1/2013 | Tokuda et al. |
| 2013/0034408 A1 | 2/2013 | Maloney |
| 2013/0136838 A1 | 5/2013 | San Miguel et al. |
| 2014/0037814 A1 | 2/2014 | Quinlan |
| 2014/0087049 A1 | 3/2014 | Ankolekar |
| 2014/0272068 A1 | 9/2014 | Prakash |

FOREIGN PATENT DOCUMENTS

| | | |
|---|---|---|
| AU | 2011-203233 A1 | 7/2011 |
| CA | 1292988 | 12/1991 |

(Continued)

OTHER PUBLICATIONS

Zijie Li, Li Cai, Qingsheng Qi, and Peng George Wang. Enzymatic Synthesis of D-Sorbose and D-Psicose with Aldolase RhaD: Effect of Acceptor Configuration on Enzyme Stereoselectivity. Bioorg Med Chem Lett. Dec. 1, 2011; 21(23): 7081-7084.*

(Continued)

*Primary Examiner* — Frederick Krass
*Assistant Examiner* — Michael P Cohen
(74) *Attorney, Agent, or Firm* — RatnerPrestia

(57) ABSTRACT

A low calorie sweetener composition with sweetness synergy, providing a reduction in off-taste and a desirable temporal profile. The sweetener composition is suitable for use as a substitute for high calorie sugars. The sweetener composition may be used in food and beverage products, pharmaceutical products, nutritional product and cosmetic products.

18 Claims, 1 Drawing Sheet

(56) References Cited

FOREIGN PATENT DOCUMENTS

| | | |
|---|---|---|
| CN | 1 266 834 | 3/1985 |
| CN | 102876817 | 1/2013 |
| EP | 1 864 669 | 12/2007 |
| EP | 2 156 751 A1 | 5/2008 |
| EP | 2 098 227 A1 | 9/2009 |
| EP | 2 537 42 2 A1 | 12/2012 |
| EP | 2 548 453 | 1/2013 |
| JP | 2001-11090 | 1/2001 |
| JP | 2001 354690 | 12/2001 |
| JP | 2005-213227 | 11/2005 |
| JP | 2008-43342 | 2/2008 |
| JP | 2008 48685 | 3/2008 |
| JP | 2010 018528 A | 1/2010 |
| JP | 2010 178683 A | 8/2010 |
| JP | 4724824 | 7/2011 |
| JP | 4761424 | 8/2011 |
| JP | 2011205913 | 10/2011 |
| JP | 2013138660 | 7/2013 |
| JP | 5308585 | 10/2013 |
| JP | 5314207 | 10/2013 |
| KR | 10-0832339 B1 | 5/2008 |
| KR | 10-2011-0041910 A | 4/2011 |
| KR | 20110041910 B1 | 4/2011 |
| KR | 101106253 | 1/2012 |
| WO | WO 94/18855 | 9/1994 |
| WO | WO 9930577 A1 * | 6/1999 ............ A23F 5/243 |
| WO | WO 2007/010975 | 1/2007 |
| WO | WO 2007/010976 | 1/2007 |
| WO | WO 2008/059625 | 5/2008 |
| WO | WO 2008/102137 | 8/2008 |
| WO | WO 2011/040708 A2 | 4/2011 |
| WO | WO 2011/139959 A1 | 11/2011 |
| WO | WO 2013/036768 | 3/2013 |
| WO | WO 2013/039365 | 3/2013 |
| WO | WO 2013/081294 | 6/2013 |
| WO | WO 2014/025235 A1 | 2/2014 |

OTHER PUBLICATIONS

Nancy K. Keith, Charles E. Pettijohn, and Megan E. Keith. Discrimination tests: Evaluating context effects and respondent reliability using the switchback experimental design. Journal of Targeting, Measurement and Analysis for Marketing (2009) 17, 115-125.*

Nabors, LO (editor), Alternative Sweeteners, 3rd Edition. New York: Marcel Dekker Inc, 2001. pages 335-338, 352-353, 367-371, 373-374.*

Stephan G. Wiet and Pamela K. Beyts. Sensory Characteristics of Sucralose and other High Intensity Sweeteners. Journal of Food Science, vol. 57, No. 4, 1992, pp. 1014-1019.*

Definition of "buttercream" from Merriam Webster On-Line Dictionary, downloaded Dec. 1, 2015, from: http://www.merriam-webster.com/dictionary/buttercream.*

Notification of Transmittal of the International Search Report and the Written Opinion of the International Searching Authority, or the Declaration Issued for International Application No. PCT/GB2014/050812 , Completed May 13, 2014 and Mailed May 23, 2014.

Combined Search and Examination Report Issued for Application No. GB 1309076.6 Dated Nov. 15, 2013.

Matsuo, et al.; *Dietary D-psicose, a C-3 epimer of D-fructose, suppresses the activity of hepatic lipogenic enzymes in rats*; Asia Pacific J. Clin. Nutr. (2001) 10(3): 233-237.

Matsuo, et al.; *D-Psicose Is a Rare Sugar That Provides No Energy to Growing Rats*; J. Nutr. Sci. Vitaminol, 48, 77-80, 2002.

Doner; *Isomerization of D-Fructose by Base: Liquid-Chromatographic Evaluation and the Isolation of D-Psicose*; Carbohydrate Research, 70 (1979)209-216 © Elsevier Scientific Publishing Company.

Angyal; *The Lobry de Bruyn-Alberda van Ekenstein Transformation and Related Reactions*; Topics in Current Chemistry, vol. 215.

Bruijn, et al.; *Alkaline Degradation of Monosaccharides V: Kinetics of the Alkaline Isomerization and Degradation of Monosaccharides*; Recueil des Travaux Chimiques des Pays-Bas, 106/2, Feb. 1987.

Combined Search and Examination Report dated Aug. 21, 2014 for GB Application No. 1403030.8, 8 pgs.

Combined Search and Examination Report Issued for Application No. GB 1309077.4 Dated Nov. 15, 2013.

Combined Search and Examination Report issued for Application No. GB 1309079.0 dated Nov. 15, 2013.

Entire patent prosecution history of U.S. Appl. No. 14/212,178, filed Mar. 14, 2014, entitled, "Sweetener."

Entire patent prosecution history of U.S. Appl. No. 14/212,196, filed Mar. 14, 2014, entitled, "Sweetener."

Notification of Transmittal of International Search Report and the Written Opinion of the International Searching Authority, or the Declaration Issued for International Application No. PCT/GB2014/050813, Completed May 13, 2014 and mailed May 23, 2014.

Notification of Transmittal of the International Search Report and the Written Opinion of the International Searching Authority, or the Declaration Issued for International Application No. PCT/GB2014/050814 , Completed May 14, 2014 and Mailed Jun. 23, 2014.

Entire patent prosecution history of U.S. Appl. No. 14/775,336, filed, Sep. 11, 2015, entitled, "Improved Sweetener."

Entire patent prosecution history of U.S. Appl. No. 14/777,047, filed, Sep. 15, 2015, entitled, "Improved Sweetener."

Entire patent prosecution history of U.S. Appl. No. 14/777,157, filed, Sep. 15, 2015, entitled, "Improved Sweetener."

Non-Final Office Action mailed Oct. 16, 2015 in U.S. Appl. No. 14/212,196.

International Preliminary Report on Patentability for International Application No. PCT/GB2014/050812 mailed Sep. 15, 2015.

International Preliminary Report on Patentability for International Application No. PCT/GB2014/050813 mailed Sep. 15, 2015.

International Preliminary Report on Patentability for International Application No. PCT/GB2014/050814 mailed Sep. 15, 2015.

Final Office Action mailed May 21, 2015 in U.S. Appl. No. 14/212,178.

Final Office Action for U.S. Appl. No. 14/212,196, mailed Jun. 16, 2016, 25 pages.

Non Final Office Action for U.S. Appl. No. 14/775,336, mailed Jun. 8, 2016, 25 pages.

Hemback, J., "Determination of the GRAS Status of the Use of Luo Han Fruit Concentrate as Flavor Modifier and Sweetener," Jul. 2009, 110 pages.

Wang, et al., "Cucurbitane Glycosides Derived from Mogroside IIE: Structure-Taste Relationships, Antioxidant Activity, and Acute toxicity,", Molecules, 2014, vol. 19, pp. 12676-12689.

* cited by examiner

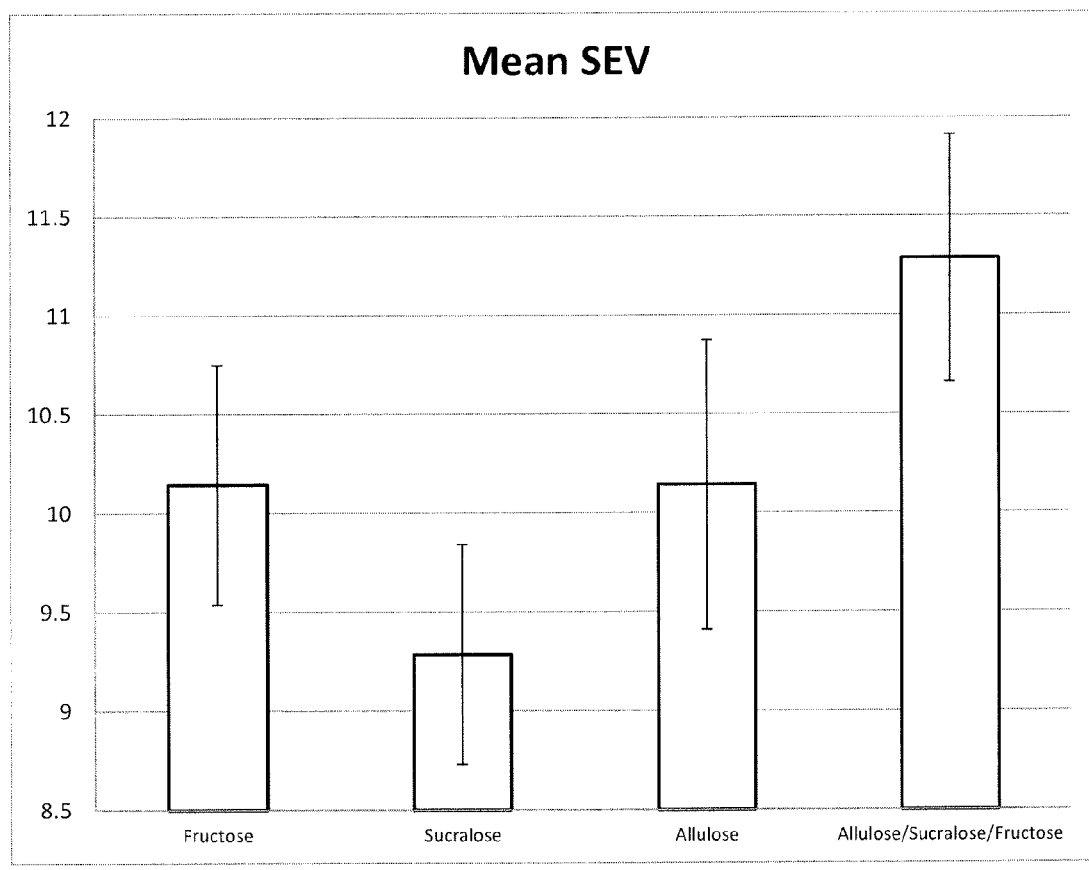

SWEETENER

CROSS REFERENCE TO RELATED APPLICATION

This application claims priority to U.S. Provisional Application No. 61/793,502 filed Mar. 15, 2013, which is incorporated herein by reference in its entirety for all purposes.

FIELD OF THE INVENTION

The present invention relates to a low calorie sweetener composition having sweetness synergy. The present invention also relates to food or beverage products comprising said sweetener composition.

BACKGROUND OF THE INVENTION

Many food and beverage products contain nutritive sweeteners such as sucrose (generally referred to as 'sugar' or 'table sugar'), glucose, fructose, corn syrup, high fructose corn syrup and the like. Such sweeteners supply not only sweetness to the food and beverage products, but also bulk, texture and desirable functional properties such as browning, humectancy, freezing point depression and the like. They also produce a favorable sensory response, for example in terms of quality of sweetness, lack of bitterness and off taste, desirable temporal profile and desirable mouthfeel.

Although desirable in terms of taste and functional properties, excess intake of nutritive sweeteners, such as sucrose, has long been associated with an increase in diet-related health issues, such as obesity, heart disease, metabolic disorders and dental problems. This worrying trend has caused consumers to become increasingly aware of the importance of adopting a healthier lifestyle and reducing the level of nutritive sweeteners in their diet.

In recent years, there has been a movement towards the development of replacements for nutritive sweeteners, with a particular focus on the development of low or zero-calorie sweeteners. An ideal replacement for a nutritive sweetener is a sweetener that has the same desirable taste characteristics and functional properties as the nutritive sweetener, but which also has fewer calories. Aiming to meet this growing need, the market has been flooded with possible candidates to replace conventional nutritive sweeteners. Unfortunately, however, many of the low or zero calorie replacements offered on the market lack one or all of the necessary characteristics, and often exhibit bitterness or off-taste. Therefore, many of the proposed sweeteners are not an ideal replacement for nutritive sweeteners.

One proposed alternative to nutritive sweeteners is allulose (also known as D-psicose). Allulose is known as a "rare sugar", since it occurs in nature in only very small amounts. It provides around 70% of the sweetness of sucrose, but only around 5% of the calories (approximately 0.2 kcal/g). It may therefore essentially be considered to be a 'zero calorie' sweetener.

In view of its scarcity in nature, production of allulose relies on the epimerization of readily available fructose. Ketose-3-epimerases can interconvert fructose and allulose, and various ketose-3-epimerases are known for carrying out this conversion.

U.S. Pat. No. 8,030,035 and PCT Publication No. WO2011/040708 disclose that D-psicose (an alternative name for allulose) can be produced by reacting D-fructose with a protein derived from *Agrobacterium tumefaciens*, and having psicose 3-epimerase activity.

US Patent Publication No. 2011/0275138 discloses a ketose 3-epimerase derived from a microorganism of the *Rhizobium* genus. This protein shows a high specificity to D- or L-ketopentose and D- or L-ketohexose, and especially to D-fructose and D-psicose. This document also discloses a process for producing ketoses by using the protein.

Korean Patent No. 100832339 discloses a *Sinorhizobium* YB-58 strain which is capable of converting fructose into psicose (i.e. allulose), and a method of producing psicose using a fungus body of the *Sinorhizobium* YB-58 strain.

Korean Patent Application No. 1020090098938 discloses a method of producing psicose using *E. coli* wherein the *E. coli* expresses a polynucleotide encoding a psicose 3-epimerase.

Allulose is present in processed cane and beet molasses, steam-treated coffee, wheat plant products and high fructose corn syrup. D-allulose is the C-3 epimer of D-fructose and the structural differences between allulose and fructose result in allulose not being metabolized by the human body to any significant extent, and thus having "zero" calories. Thus, allulose is thought to be a promising candidate as a replacement for nutritive sweeteners and as a sweet bulking agent, as it has no calories and is reported to be sweet while maintaining similar properties to sucrose. However, the use of allulose alone as a replacement for nutritive sweeteners may have some limitations due to cost and digestive tolerance in some applications.

Alternative sweeteners on the market include sucralose and fructose. Sucralose is a 'high potency' or 'high intensity' sweetener that is approximately 600 times as sweet as sucrose. Fructose (also known as "fruit sugar") is a 6-carbon polyhydroxyketone monosaccharide sugar that is often found in plants and in honey. The monosaccharide is found in crystalline form, often referred to as D-fructose. Fructose can also be found as a component of other sweeteners such as high-fructose corn syrup (HFCS), which is a mixture of glucose and fructose. Fructose is frequently used to enhance the sweetness and taste of food and beverage products. Using fructose as a replacement for sucrose and other nutritive sweeteners also has its limitations, as fructose is fully caloric and thus does not provide an effective calorie reduction strategy.

Therefore, there is a need to provide an improved replacement for nutritive sweeteners that has low calories and is without limitations in use, but which also has taste characteristics and functional properties similar to those of sucrose and other nutritive sweeteners.

SUMMARY OF THE INVENTION

The present invention seeks to provide a solution to the above-mentioned problem by providing a sweetener composition having taste characteristics comparable to sucrose but having low calories. Advantageously, the present invention also seeks to provide a sweetener composition having sweetness synergy, a reduction in off-taste or off-flavor, a desirable temporal profile and improved mouthfeel, compared with proposed sweeteners currently available on the market.

A first aspect of the present invention provides a sweetener composition comprising allulose, fructose and sucralose.

According to an embodiment, the sweetener composition comprises allulose in an amount of about 45% to about 80%, fructose in an amount of about 20% to about 55%, and sucralose in an amount of about 0.02% to about 0.3% by weight relative to the total weight of the composition.

According to another embodiment, the sweetener composition comprises allulose in an amount of about 61.4%, fructose in an amount of about 38.4%, and sucralose in an amount of about 0.2%, by weight relative to the total weight of the composition.

According to another embodiment, the sweetener composition comprises allulose in an amount of about 77.4%, fructose in an amount of about 22.5%, and sucralose in an amount of about 0.05% by weight relative to the total weight of the composition.

According to another embodiment, the sweetener composition comprises allulose in an amount of about 46.1%, fructose in an amount of about 53.8%, and sucralose in an amount of about 0.06% by weight relative to the total weight of the composition.

In some embodiments, the sweetener composition further comprises a sweet taste improving additive, a bulking agent, a flavoring agent, and/or a stabilizer.

A further aspect of the present invention provides a food or beverage product comprising the sweetener composition of the invention.

A further aspect of the present invention provides a table-top sweetener comprising the sweetener composition of the invention.

Further aspects of the present invention provide: a bulking agent comprising a sweetener composition according to the invention; a coating agent comprising a sweetener composition according to the invention; a cosmetic product comprising a sweetener composition according to the invention; a pharmaceutical product comprising a sweetener composition according to the invention; a nutritional product comprising a sweetener composition according to the invention; and a sports product comprising a sweetener composition according to the invention.

Another aspect of the present invention provides the use of a sweetener composition according to the present invention in a food product, a beverage product, a pharmaceutical product, a nutritional product, a sports product, or a cosmetic product. Another aspect of the present invention provides the use of a sweetener composition according to the present invention as a bulking agent. Another aspect of the present invention provides the use of a sweetener composition according to the present invention as a coating agent.

DETAILED DESCRIPTION OF THE FIGURES

FIG. 1: Graph illustrating the Mean SEV for allulose, fructose, sucralose and a composition comprising allulose, fructose and sucralose.

DETAILED DESCRIPTION OF THE INVENTION

The present invention is based on the surprising finding that allulose, fructose and sucralose exhibit sweetness synergy, whereby the blend is sweeter than the expected sweetness based on the sweetness of its components. That is to say, the relative sweetness of the sweetener composition is greater than the sweetness calculated from the individual components of the composition.

Furthermore, it has been found that this blend of allulose, fructose and sucralose addresses problems associated with the individual components, in particular, with regard to off-flavor and/or undesirable temporal profile. In addition, due to the presence of the zero calorie sweeteners, allulose and sucralose, the sweetener composition is low calorie. Furthermore, as a consequence of the sweetness synergy exhibited by the composition, the amount of the composition required to provide a given level of sweetness is less than would be expected in the absence of synergy, thereby allowing a further reduction in calories. Thus, a sweetener composition according to the present invention provides enhanced sweetness, improves the balance of flavor by reducing off-taste or off-flavor, and provides a more desirable temporal profile, while at the same time allowing a significant reduction in calories compared to a sweet-equivalent amount of a conventional nutritive sweetener.

Using a sweetener composition according to the present invention allows delivery of an increased sweetness in food or beverage products when compared to the individual components used separately. This enhanced sweetness means that a smaller amount of sweetener can be used in these products, to provide a temporal and taste profile that closely matches that of sucrose.

In general terms, the present invention relates to a sweetener composition comprising the sweeteners allulose, fructose and sucralose.

The term "allulose" as used herein refers to a monosaccharide sugar of the structure shown as a Fischer projection in below Formula I. It is also known as "D-psicose":

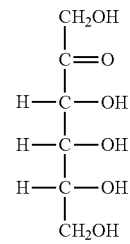

Formula (I)

The term "fructose" as used herein refers to the monosaccharide sugar of the structure shown as a Fischer projection in below Formula II:

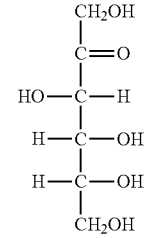

Formula (II)

The term "sucralose" as used herein refers to sucralose of the structure shown in Formula III:

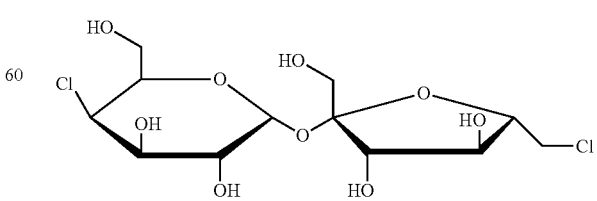

Formula (III)

The term "temporal profile" of a composition, sugar or sweetener, as used herein, is a measure of the perceived sweetness intensity of said composition, sugar or sweetener over time. A desirable or advantageous temporal profile is one wherein sweetness is observed quickly and has a short linger similar to that of sucrose.

The term "sucrose equivalent value" or "SEV" as used herein refers to the sweetness equivalent of a sweetener related to the sweetness of sucrose. For example, a sweetener at an SEV value of 5 would have a sweetness similar to a 5% by weight solution of sucrose.

The term "low calorie" as used herein refers to a sweetener having 40 calories or fewer per reference amount customarily consumed (RACC) and per labeled serving.

All amounts given in % by weight are quoted on a dry solids (ds) basis unless specifically stated otherwise. Thus, where components are provided other than in their pure form, the amount added should be adjusted to provide the required amount on a dry solids basis. For example, where allulose is provided as a syrup, the amount of syrup used should be adjusted to supply the required amount of allulose on a dry solids basis.

One embodiment of the present invention provides a sweetener composition comprising allulose, fructose and sucralose.

According to another embodiment of the present invention, the sweetener composition comprises allulose in an amount of about 45% to about 80%, fructose in an amount of about 20% to about 55%, and sucralose in an amount of about 0.02% to about 0.3% by weight relative to the total weight of the composition.

Preferably, the sweetener composition of the invention comprises allulose in an amount of about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% or 80%, fructose in an amount of about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55%, and sucralose in an amount of about 0.05, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, or 0.30%, by weight relative to the total weight of the composition.

It is particularly preferred that the sweetener composition comprises allulose in an amount of about 61.4% (preferably, about 55% to about 70%, or about 60% to about 63%), fructose in an amount of about 38.4% (preferably, about 30% to about 45%, or about 36% to about 40%), and sucralose in an amount of about 0.2% (preferably, about 0.1% to about 0.25%, or about 0.18% to about 0.22%) by weight relative to the total weight of the composition. In a another preferred embodiment of the present invention, the sweetener composition comprises allulose in an amount of about 77.4% (preferably, about 70% to about 80%, or about 75% to about 79%), fructose in an amount of about 22.5% (preferably, about 15% to about 30%, or about 20% to about 24%), and sucralose in an amount of about 0.05% (preferably, about 0.02% to about 0.1%, or about 0.03% to about 0.07%) by weight relative to the total weight of the composition. In an alternative embodiment of the present invention, the sweetener composition comprises allulose in an amount of about 46.1% (preferably, about 40% to about 55%, or about 42% to about 49%), fructose in an amount of about 53.8% (preferably, about 45% to about 55%, or about 52% to about 55%), and sucralose in an amount of about 0.06% (preferably, about 0.02% to about 0.1%, or about 0.04% to about 0.08%) by weight relative to the total weight of the composition In another embodiment of the present invention, two of the components of the sweetener composition, selected from allulose, fructose and sucralose, are present in an amount of about 25% (by percentage of added sweetness in terms of relative sugar equivalent value (SEV)) and the remaining component is present in an amount of about 50% (by percentage of added sweetness in terms of relative sugar equivalent value (SEV)).

Advantageously, the sweetener composition comprises allulose in an amount of about 25%, fructose in an amount of about 25%, and sucralose in an amount of about 50% (by percentage of added sweetness in terms of relative sugar equivalent value (SEV)). In an alternative embodiment, the sweetener composition comprises allulose in an amount of about 50%, fructose in an amount of about 25% and sucralose in an amount of about 25% (by percentage of added sweetness in terms of relative sugar equivalent value (SEV)). The sweetener may, alternatively, comprise allulose in an amount of about 25%, fructose in an amount of about 50% and sucralose in an amount of about 25% (by percentage of added sweetness in terms of relative sugar equivalent value (SEV)).

In some embodiments, the sweetener composition may further comprise a sweet taste improving additive, a bulking agent, a flavoring agent, and/or a stabilizer.

A further aspect of the present invention provides a food product comprising a sweetener composition according to the invention. Non-limiting examples of a food product include a confectionary product, a dessert product such as, yogurt, ice-cream, biscuits, cakes, a cereal product, baked goods, frozen dairy products, meats, dairy products, condiments, snack bars, soups, dressings, mixes, prepared foods, baby foods, diet preparations, syrups, food coatings, dried fruit, sauces, gravies, jams/jellies, and the like, especially those which are reduced sugar or low sugar products. The food product may be an animal feed product. A food product according to the invention may comprise a sweetener composition as a coating or frosting formed on the surface of the product. This coating improves the flavor of the food product as well as its shelf life.

Another aspect of the invention provides a beverage product comprising a sweetener composition according to the present invention. Non-limiting examples of a beverage product include a carbonated beverage, a non-carbonated beverage, fruit-flavored beverage, fruit-juice, tea, milk, coffee, especially those which are reduced sugar or low sugar products.

A further aspect of the present invention provides a table-top sweetener comprising a sweetener composition according to the invention.

Another aspect of the present invention provides a bulking agent comprising a sweetener composition according to the invention.

Another aspect of the present invention provides a coating agent comprising a sweetener composition according to the invention.

Another aspect of the present invention provides a pharmaceutical product comprising a sweetener composition according to the invention.

Another aspect of the present invention provides a nutritional or sports product comprising a sweetener composition according to the invention.

Another aspect of the present invention provides a cosmetic product comprising a sweetener composition according to the invention.

It will be appreciated that the amount of a sweetener composition according to the invention present in a food product, a beverage product, a pharmaceutical product, a nutritional product, a sports product, or a cosmetic product, will depend upon the type and amount of sweetener present in the sweetener composition and the desired sweetness of the food or beverage product.

An alternative aspect of the present invention provides the use of a sweetener composition according to the invention in a food product, a beverage product, a pharmaceutical product, a nutritional product, a sports product, or a cosmetic product, as a bulking agent or as a coating agent.

The sweetener composition may be formulated in any ingestible form, for example, as a syrup, in powder form, tablet form, as granules, in a solution or in any other suitable form including beverages and food products.

As outlined in the below example, a sweetener composition according to the present invention exhibits an unexpected sucrose equivalent value (SEV) greater than the predicted value based on its individual components. Therefore, a sweetener composition according to the present invention displays sweetness synergy.

The following example is exemplary only and is not intended to be limiting in any way.

Example

Demonstration of Sweetness Synergy of the Composition of the Present Invention

Materials and Methods

Round table evaluations were performed with test panelists. Equal sweet 10 SEV concentrations in neutral pH water were made for allulose, fructose and sucralose, as well as a composition comprising allulose, fructose and sucralose. The components of the test compositions are described in the below tables. The mixed compositions were calculated using the Beidler mixture equation for the sweeteners. The Beidler mixture equation for sweeteners is as follows:

$$SEV = \frac{conc \cdot R_{max}}{conc + 1/K}$$

The concentration of each component in the mixture in ppm is divided by SEV (c/R) and is plotted against concentration, c. The slope of the linear regression is the maximum SEV ($R_{max}$). The y-intercept of the linear regression multiplied by $R_{max}$ is the half-maximal sweetness concentration, $1/K$. $R_{max}$ and $1/K$ are the two parameters used in the Beidler equation.

The equal-molar mixture was tested against reference samples for the panelists to determine SEV values. References samples were 4%, 6%, 8%, 10%, 12%, and 14% sucrose in neutral pH water. The test samples were served in 2 ounce (approximately 60 ml) soufflé cups coded with 3-digit codes at room temperature. A two minute wait period between samples was enforced. Water and unsalted crackers was available for the panelists to clear their palates before and during testing. EyeQuestion, software distributed by Logic8 BV of Elst, The Netherlands, was used for ballot development and recording of results. Results were collected in EyeQuestion for calculating approximate SEV level of each test sample. The test products analyzed in this experiment are described below in Table 1.

Product Information

TABLE 1

| INGREDIENT | Allulose 10% % | Allulose 10% GRAMS | Sucralose SEV 10 % | Sucralose SEV 10 GRAMS | Fructose SEV 10 % | Fructose SEV 10 GRAMS | Allulose/Fructose/ Sucralose % | Allulose/Fructose/ Sucralose GRAMS |
|---|---|---|---|---|---|---|---|---|
| Allulose 89% DS syrup | 17.02 | 40.848 | 0 | 0 | 0 | 0 | 5.6733 | 13.616 |
| Sucralose | 0 | 0 | 0.0237 | 0.05688 | 0 | 0 | 0.0079 | 0.01896 |
| Fructose | 0 | 0 | 0 | 0 | 8.55 | 20.52 | 2.85 | 6.84 |
| RO Water | 82.98 | 199.152 | 99.9763 | 240 | 91.45 | 219.48 | 91.468 | 219.525 |
| TOTAL | 100 | 240 | 100 | 240 | 100 | 240 | 100 | 240 |

Results

FIG. 1 illustrates the mean sucrose equivalent values for the sweetener composition of the present invention as well as the SEV for each of the individual components of the sweetener composition.

Table 2 recites the mean and median sucrose equivalent values (SEV) for the sweetener composition of the present invention as well as the SEV for each of the individual components of the sweetener composition.

TABLE 2

| | Mean 1 | StDev | Median 1 | 1 STDEV |
|---|---|---|---|---|
| Fructose | 10.14286 | 1.214986 | 10 | 0.607493 |
| Sucralose | 9.285714 | 1.112697 | 10 | 0.556349 |
| Allulose | 10.14286 | 1.46385 | 10 | 0.731925 |
| Allulose/ Fructose/ Sucralose | 11.28571 | 1.253566 | 11 | 0.626783 |

| | Allulose(A) | Sucralose(C) | Fructose(D) | Allulose/ Sucralose/ Fructose(G) |
|---|---|---|---|---|
| Sweetness | 10.14 | 9.29 | 10.14 | 11.29$^{b-c}$ |

Level of Significance (Duncan): A' <99.9%; A <99, %; a <95%; a' <90%
The ANOVA performed is a two-way ANOVA

| Sweetness | 10.14$^{b-c}$ | 9.29$^{c}$ | 10.14$^{b-c}$ | 11.29$^{a-b}$ |
|---|---|---|---|---|

Level of significance for the grouping (Duncan): 5%

The sweetener composition comprising allulose, fructose and sucralose was significantly sweeter than Sucralose at a 95% CI, and significantly sweeter than allulose and Fructose components at a 90% CI. Therefore, a composition according to the present invention surprisingly exhibits a sweetness greater than the predicted sweetness based on its individual components.

CONCLUSION

The sweetener composition of the present invention exhibits a statistically significant sweetness synergy.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A sweetener composition comprising allulose in an amount of about 45% to about 80%, fructose in an amount of about 20% to about 55% and sucralose in an amount of about 0.02% to about 0.3% by weight relative to the total weight of the composition.

2. The sweetener composition according to claim 1, comprising allulose in an amount of about 61.4%, fructose in an amount of about 38.4%, and sucralose in an amount of about 0.2% by weight relative to the total weight of the composition.

3. The sweetener composition according to claim 1, comprising allulose in an amount of about 77.4%, fructose in an amount of about 22.5%, and sucralose in an amount of about 0.05% by weight relative to the total weight of the composition.

4. The sweetener composition according to claim 1, comprising allulose in an amount of about 46.1%, fructose in an amount of about 53.8%, and sucralose in an amount of about 0.06% by weight relative to the total weight of the composition.

5. The sweetener composition according to claim 1, further comprising at least one of a sweet taste improving additive, a bulking agent, a flavoring agent, and a stabilizer.

6. A food product comprising the sweetener composition according to claim 1.

7. The food product of claim 6, wherein the sweetener composition is provided as a coating or frosting on the surface of the food product.

8. A beverage product comprising the sweetener composition according to claim 1.

9. A table-top sweetener comprising the sweetener composition according to claim 1.

10. A bulking agent comprising the sweetener composition according to claim 1.

11. A coating agent comprising the sweetener composition according to claim 1.

12. A cosmetic product comprising the sweetener composition according to claim 1.

13. A pharmaceutical product comprising the sweetener composition according to claim 1.

14. A nutritional product comprising the sweetener composition according to claim 1.

15. A sports product comprising the sweetener composition according to claim 1.

16. A method of manufacturing a reduced-calorie product comprising adding the sweetener composition according to claim 1 to a food product, a beverage product, a pharmaceutical product, a nutritional product, a sports product, or a cosmetic product.

17. A method of increasing bulk of a product comprising adding a bulking agent comprising the sweetener composition according to claim 1 to the product.

18. A method of coating a product comprising applying a coating agent comprising the sweetener composition according to claim 1 to the product.

* * * * *